US008347730B2

(12) United States Patent
Lorenz et al.

(10) Patent No.: US 8,347,730 B2
(45) Date of Patent: Jan. 8, 2013

(54) SUBSTANTIALLY FLEXIBLE IMPLANT HOLDER FOR A TUBULAR IMPLANT STRUCTURE

(75) Inventors: Markus Lorenz, Karlsruhe (DE); Thiemo Blank, Plankstadt (DE); Roman Forreiter, Ettlingen (DE)

(73) Assignee: C. R. Bard, Inc., Murray Hill, NJ (US)

( * ) Notice: Subject to any disclaimer, the term of this patent is extended or adjusted under 35 U.S.C. 154(b) by 809 days.

(21) Appl. No.: 12/438,231

(22) PCT Filed: Aug. 14, 2007

(86) PCT No.: PCT/EP2007/058400
§ 371 (c)(1),
(2), (4) Date: Jul. 10, 2009

(87) PCT Pub. No.: WO2008/022942
PCT Pub. Date: Feb. 28, 2008

(65) Prior Publication Data
US 2010/0000329 A1 Jan. 7, 2010

(30) Foreign Application Priority Data
Aug. 22, 2006 (GB) .................................. 0616662.3

(51) Int. Cl.
*G01N 3/02* (2006.01)
(52) U.S. Cl. ........................................................ 73/856
(58) Field of Classification Search ............. 73/856, 73/818
See application file for complete search history.

(56) References Cited

U.S. PATENT DOCUMENTS

2004/0016301 A1   1/2004   Moreno et al.
2006/0211984 A1*  9/2006   Blank et al. .............. 604/102.02

FOREIGN PATENT DOCUMENTS

DE   19903476 A1   8/2000
WO   03009780 A2   2/2003

OTHER PUBLICATIONS

EP 07802597.0 filed Aug. 14, 2007 Office Action dated Dec. 22, 2010.
PCT/EP2007/058400 filed Aug. 14, 2007 International Preliminary Report on Patentability dated Feb. 24, 2009.
PCT/EP2007/058400 filed Aug. 14, 2007 Search Report dated Mar. 3, 2008.
PCT/EP2007/058400 filed Aug. 14, 2007 Written Opinion dated Mar. 3, 2008.

* cited by examiner

*Primary Examiner* — Lisa Caputo
*Assistant Examiner* — Jamel Williams
(74) *Attorney, Agent, or Firm* — Rutan & Tucker, LLP

(57) ABSTRACT

A substantially flexible implant holder for holding a substantially tubular implant structure during fatigue testing of the implant structure, the implant holder having a substantially elongate cavity for occupation by the tubular implant structure and a cavity-surrounding part which extends from at least a first longitudinal end of the cavity to at least a second longitudinal end of the cavity, the cavity-surrounding part having a stiffness which gradually changes from a relatively high stiffness adjacent each of the longitudinal ends of the cavity to a relatively low stiffness adjacent a middle portion which is situated between the two longitudinal ends of the cavity.

25 Claims, 13 Drawing Sheets

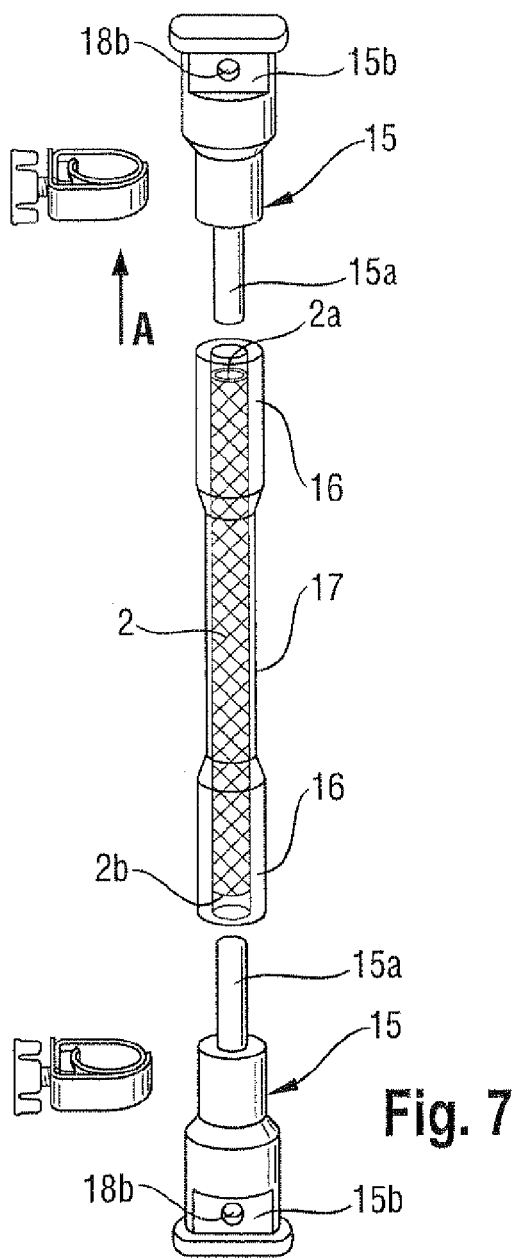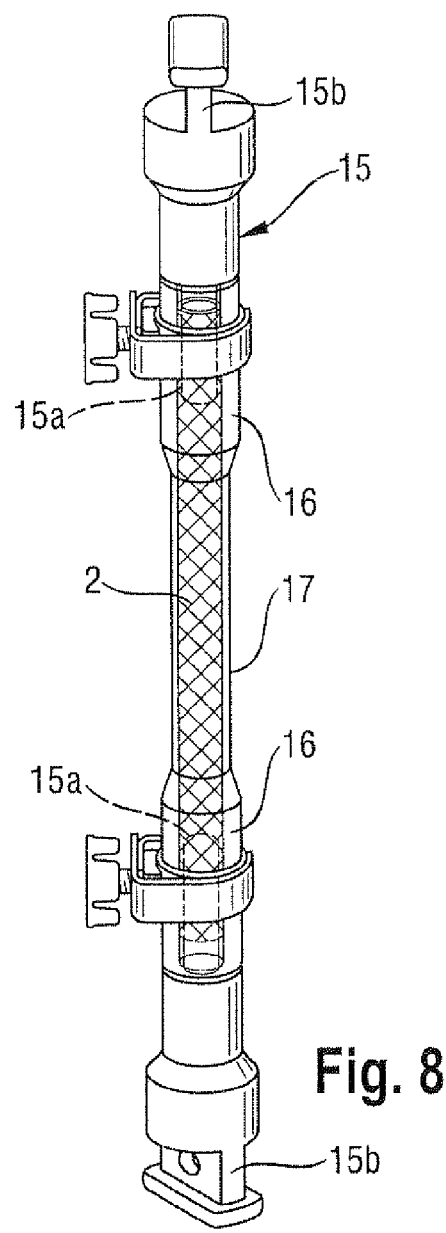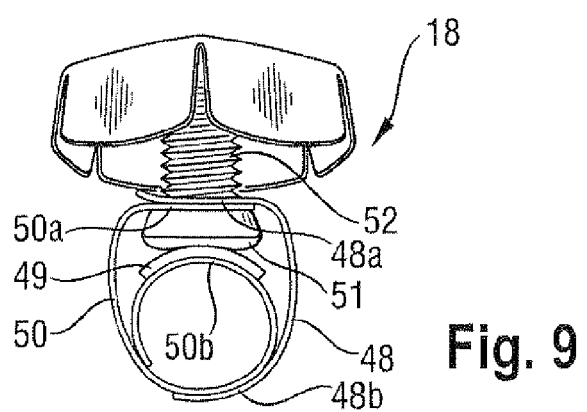

SUBSTANTIALLY FLEXIBLE IMPLANT HOLDER FOR A TUBULAR IMPLANT STRUCTURE

PRIORITY

Figure 1:
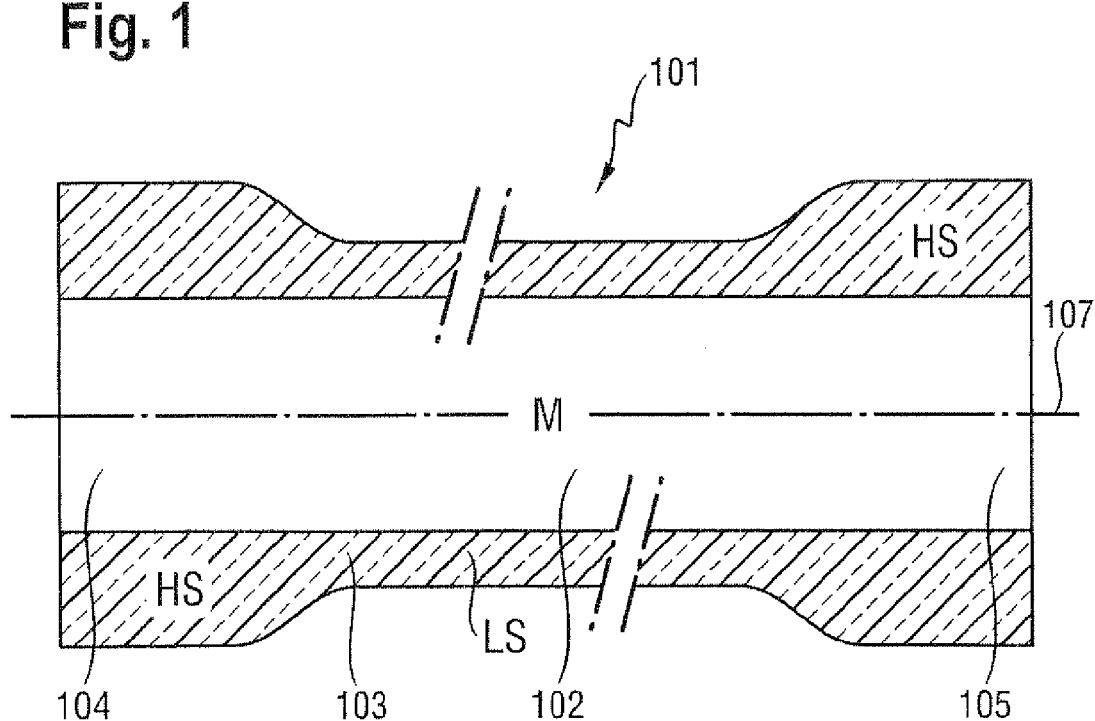

This application is a U.S. national stage application under 35 USC §371 of International Application No. PCT/EP2007/058400, filed Aug. 14, 2007, claiming priority to Great Britain Patent Application No. filed Aug. 22, 2006, each of which is incorporated by reference in its entirety into this application.

FIELD OF THE INVENTION

The invention is related to a substantially flexible implant holder for holding a substantially tubular implant structure during fatigue testing of the implant structure.

The invention is further related to use of a substantially flexible holder for holding a substantially tubular implant structure during fatigue testing that implant structure.

BACKGROUND OF THE INVENTION

A tubular implant structure is well known in, for instance, the field of intraluminally deliverable implants and is usually within a radial range and within an axial range expandable and contractable. A so-called "stent" is a well known example of such a structure. Such a structure is usually introduced into the body of a human or an animal and delivered to a site within that body where the tubularity of the structure can play a crucial role in the functioning of at least that part of the body. That part is usually a part of the vascular system of the body, but can also be a part of another system of the body, for instance the biliary system or the digestive system.

A catheter is often used for delivery at the implant site. Whilst being delivered, the diameter of the tubular implant structure is preferably as small as possible. Currently, the diameter can be as small as 6-5 French (three French being equal to 1 mm). Once arrived at the implant site, the tubular implant structure is usually made to expand so that its diameter reaches a diameter within a predetermined range, for instance 18-24 F. Given these transformations, it will be appreciated that the tubular implant structure is often a complex device comprising struts connected in a sophisticated manner so that the structure can perform the required "jobs".

Referring again to the example of a stent, in the radially expanded condition, it provides a "scaffolding" that internally supports the inner wall of a lumen and helps keeping the lumen open so that the fluid flow through that lumen can continue. For the vascular system is the lumen part of a vessel and the fluid flow a blood flow.

As usually the part of the body in which the tubular implant structure has been implanted, may be subjected to various types of movement and a large number of these measurements, it is necessary to know in advance the behaviour of the implant structure when subjected to such movements and its behaviour after having been subjected to a number of such movements that may occur during the remaining lifetime of the body. In particular structures implanted in ligaments or in for instance the neck, may experience subjection to various movements, and consequently to deformations such as torsion, axial compression, axial elongation, bending, and combinations thereof.

US 2004/0016301 A1 describes a vascular prosthesis tester that is configured to subject a stent, possibly provided with a graft, to tensile and/or compressive axial loads, bending stresses, and torsional stresses. Actuators may induce the stresses independently or in combination, or in a manner to simulate physiological movement, such as walking. The test member, i.e. the stent or stent-graft, may be disposed upon the outer surface of a fluid conduit. It is also possible that the stent or stent-graft is contained within a channel of a fluid conduit. The stent or stent-graft is "friction fit" placed within or around the conduit. A fluid is injected into the central lumen of the conduit to subject the test member to stress as applied by a change of blood pressure in a vessel during the pumping of the heart. The axial movement to which the tubular implant structure, in this case the stent, is subjected during the test, depends very much on the mechanical properties of the combined structure of the tubular implant structure and the fluid conduit. It is most likely that the fluid conduit is less flexible than the tubular implant structure. In that case, the movement to which the tubular implant structure is subjected, is for a great deal dependent on the response of the fluid conduit to the movements imposed on the fluid conduit by the actuators. To impose any movement at the middle portion of the tubular implant structure, the actuators usually apply a large "stroke" to the positions of the fluid conduit which are far away from the middle portion of the tubular implant structure, and which are sometimes even far away from the ends of the tubular implant structure. The maximum "stroke" as controlled by the actuators, is then "passed on" from these controlled positions towards the middle portion of the fluid conduit and the middle portion of the tubular implant structure. A disadvantage of this method is thus that the middle portion of the tubular implant structure is relatively little subjected to movement. The outer portion of the tubular implant structure, the ends of the stent in this case, are subjected to relatively large movement. The larger the movement, the larger the deformation and the smaller the movement, the smaller the deformation. It follows that the smaller deformation occurs at the middle portion of the tubular implant structure. Fracture is likely to occur at the outer ends of the tubular implant structure rather than at the middle portion. As a result of this, it is not the design of the tubular implant structure, in this case of the stent, which is being fatigue tested, but rather the end portions which suffer from all kinds of side effects. The outcome of the test does not allow for comparing two differently designed tubular implant structures, as the response of the ends of the tubular implant structure dominate the fracture behaviour. In general make a fair comparison of fatigue behaviour between differently designed implant structures very troublesome.

It is an object of one embodiment of the invention to provide an implant holder for holding a substantially tubular implant structure during fatigue testing of the implant structure such that the middle portion of the tubular implant structure is subjected to the maximum movement rather than the outer portions of the tubular implant structure.

It is an object of one embodiment of the invention to provide an implant holder which allows for a high reproducibility of fatigue tests.

It is an object of one embodiment of the invention to provide an implant holder which allows for a fair comparison of two differently designed tubular implant structures.

It is a further object of one embodiment of the invention to provide a holder which allows for connecting a tubular implant structure to a fatigue test system so that the connection itself is unlikely to contribute to the damage the tubular implant structure experiences during fatigue testing.

SUMMARY OF THE INVENTION

A substantially flexible implant holder is provided for holding a substantially tubular implant structure during fatigue testing of the implant structure. The implant holder has a substantially elongate cavity for occupation by the tubular implant structure and a cavity-surrounding part which extends from at least a first longitudinal end of the cavity to at least a second longitudinal end of the cavity. A cavity-surrounding part has a stiffness which gradually changes from a relatively high stiffness adjacent each of the longitudinal ends of the cavity to a relatively low stiffness adjacent a middle portion which is situated between the two longitudinal ends of the cavity. As a result of the relative inflexibility of the holder adjacent the longitudinal ends of the cavity and the relative high flexibility adjacent the middle portion of the cavity, will the tubular implant structure occupying the cavity more likely to be subjected to a movement which is larger than movements of the ends of that tubular implant structure. It is therefore likely that the middle portion is the portion of the implant structure which will show damage before the end portions show damage. Consequently, the middle portion is tested rather than the end portions of the tubular implant structure. This allows for a fairer comparison of for instance stent designs as possible end effects can only marginally play a role, if at all, in comparison to the effects occurring at the middle portion of the stent.

In a sense, the fatigue test carried out using an implant holder according to the invention is a very "pure" test, allowing for a fair comparison of test results for different structures. A test carried out on a fatigue test system using an implant holder according to the invention provides conditions which meet requirements for standardization of fatigue testing of tubular implant structures such as stents.

These and other advantages of the invention will be further explained below in our description of particular embodiments.

The accompanying drawings, which are incorporated herein and constitute part of this specification, illustrate presently preferred embodiments of the invention, and, together with the general description given above and the detailed given below, serve to explain features of the invention.

SHORT DESCRIPTION OF THE DRAWING

Figure 2:
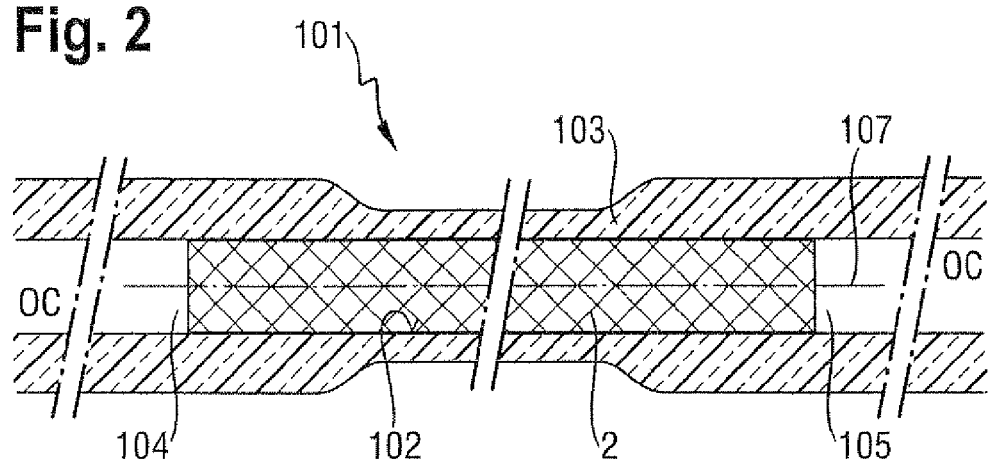
Figure 3:
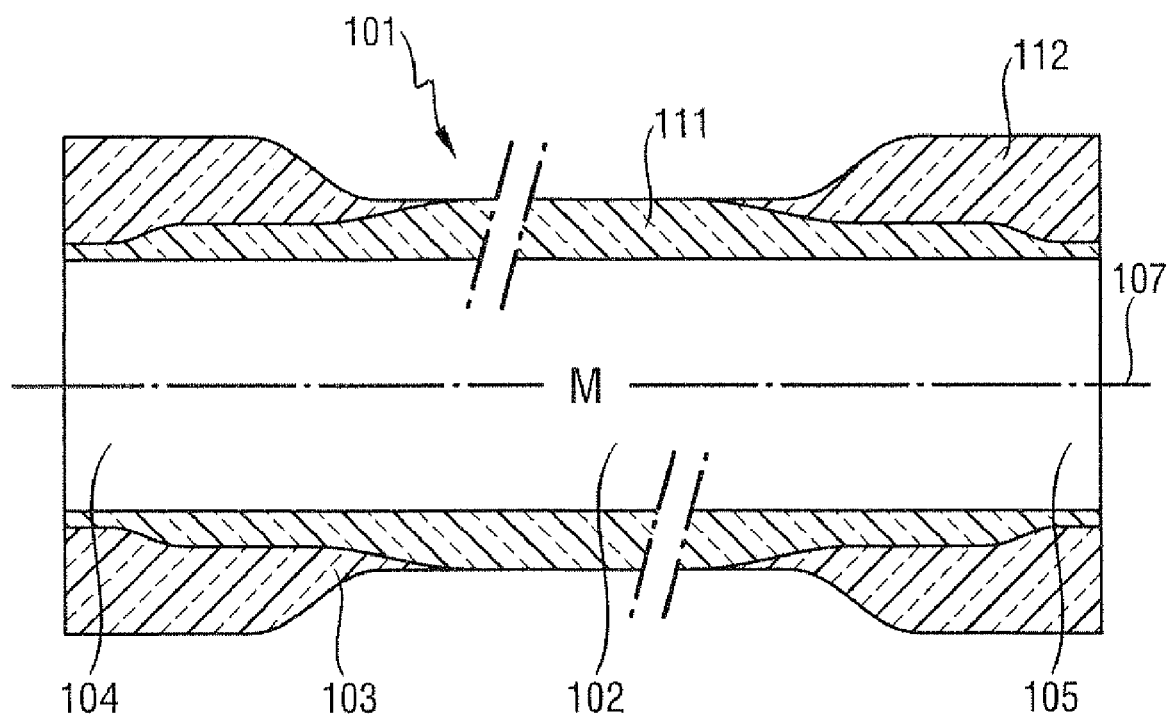
Figure 4A:
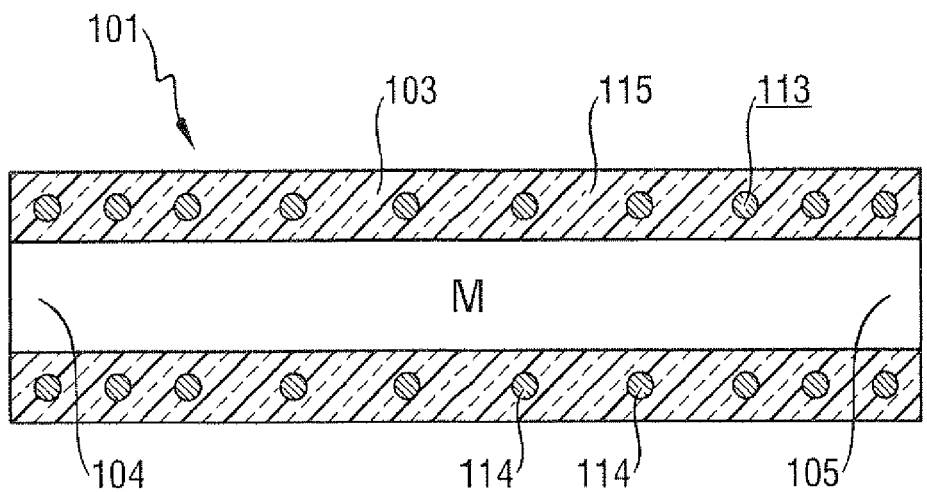
Figure 4B:
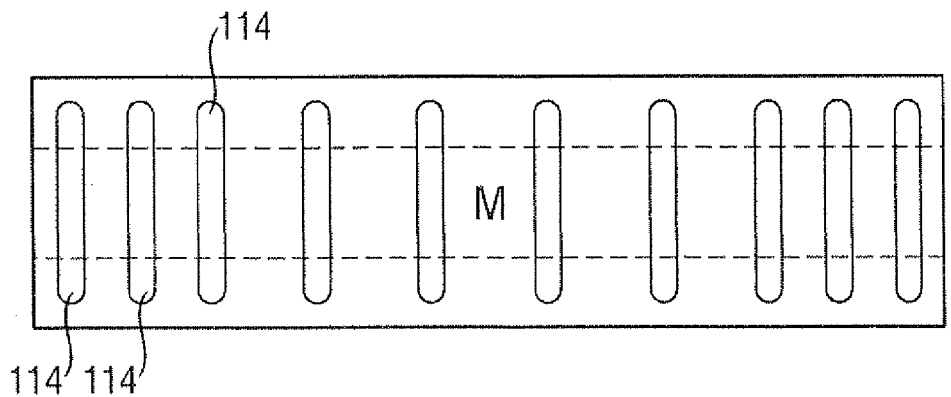
Figure 5:
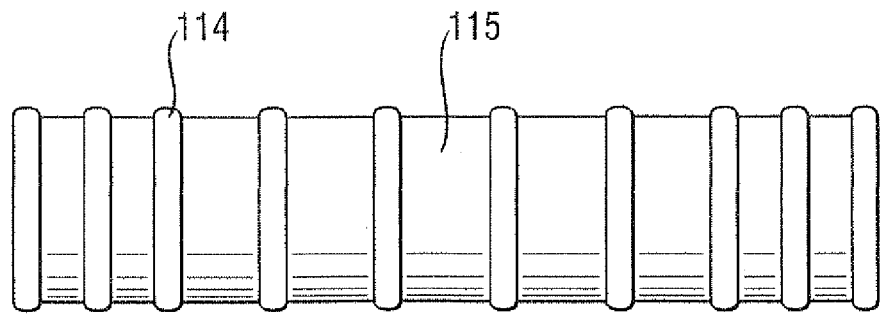
Figure 6:
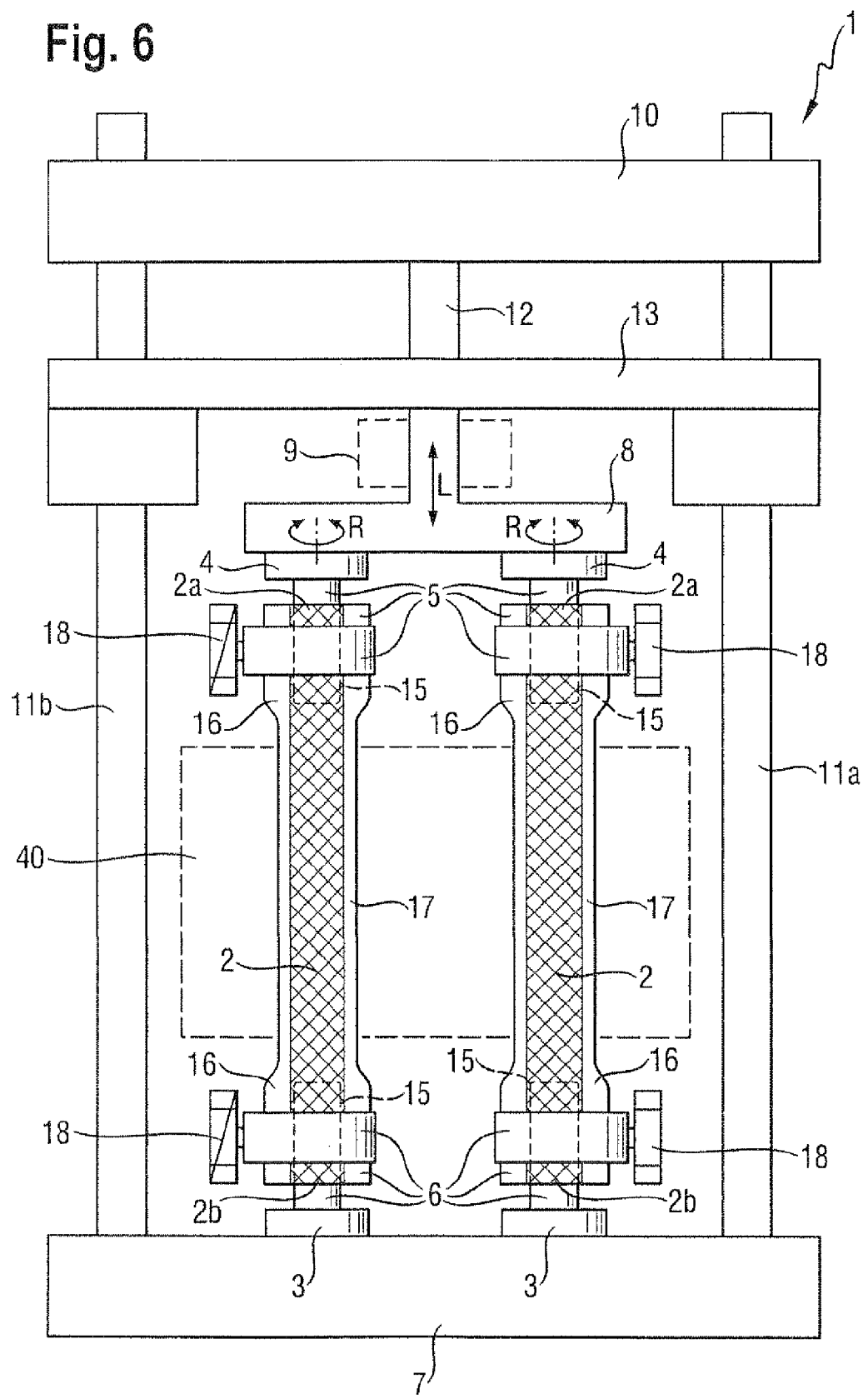
Figure 10:
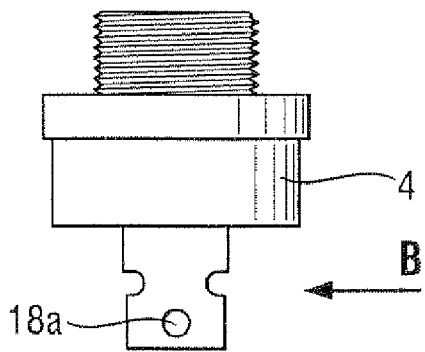
Figure 11:
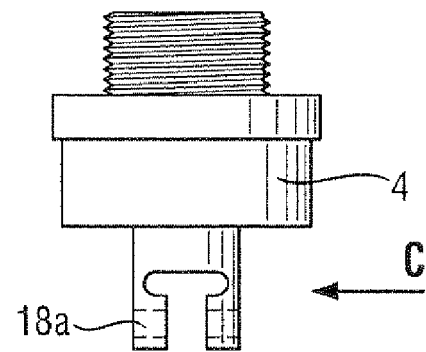
Figure 12:
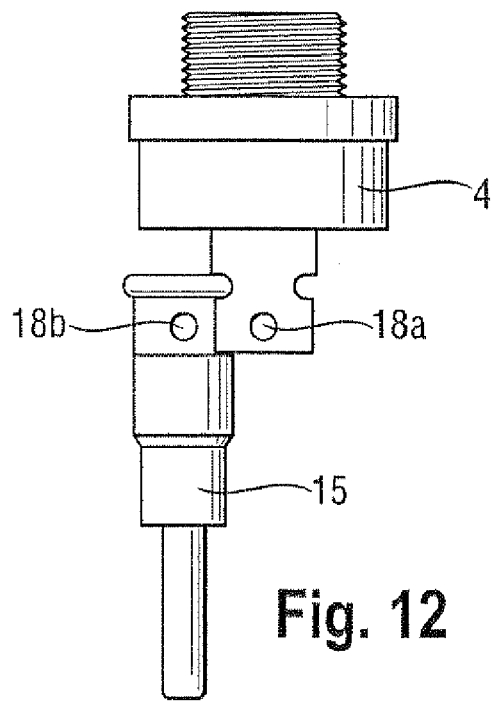
Figure 13:
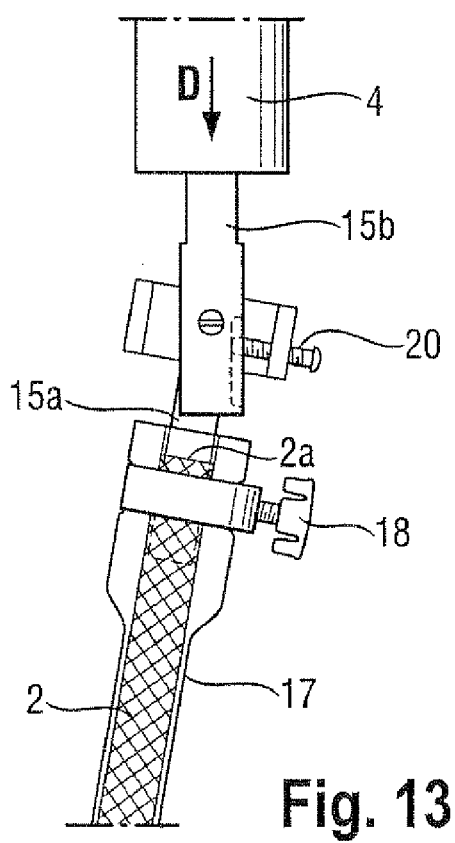
Figure 15:
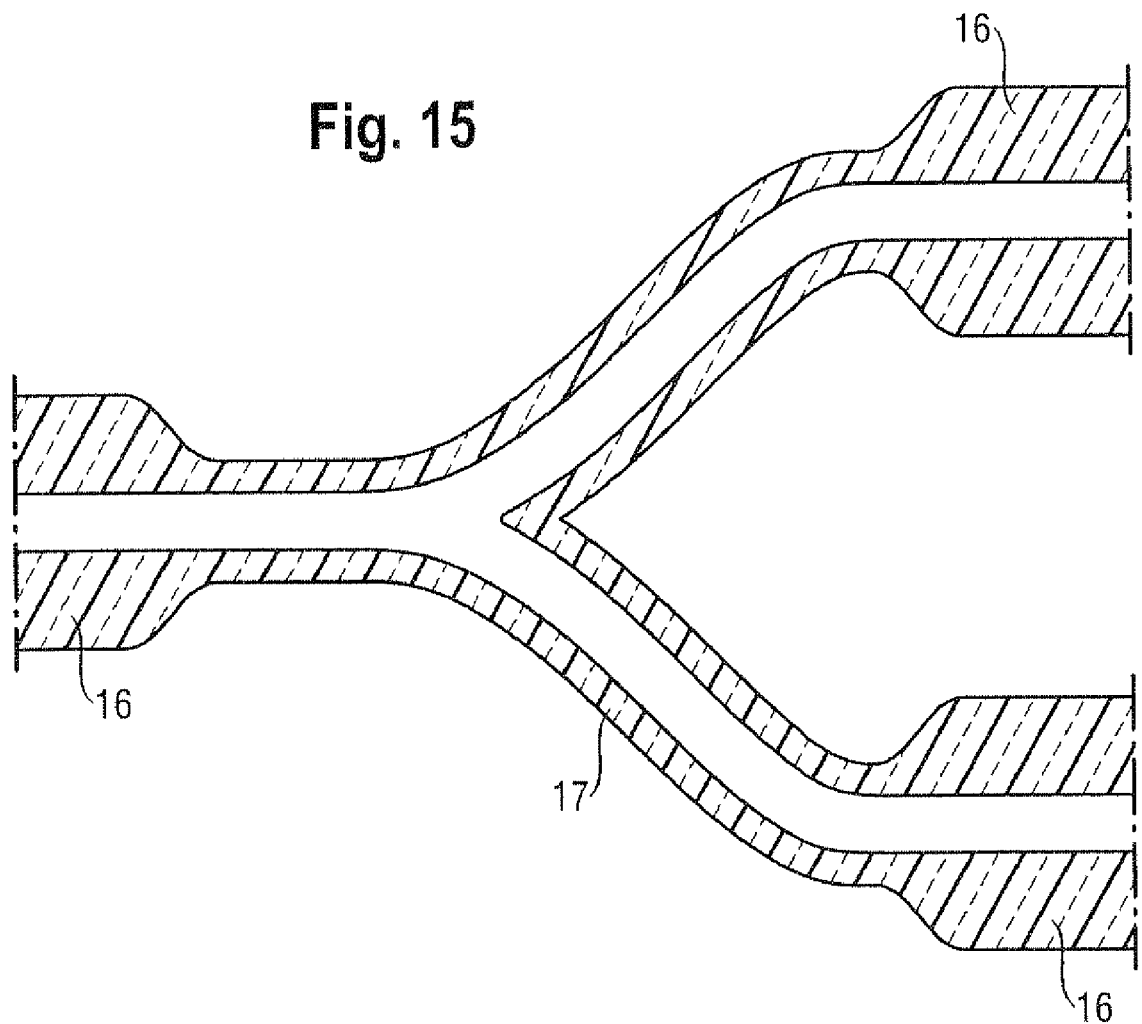
Figure 16:
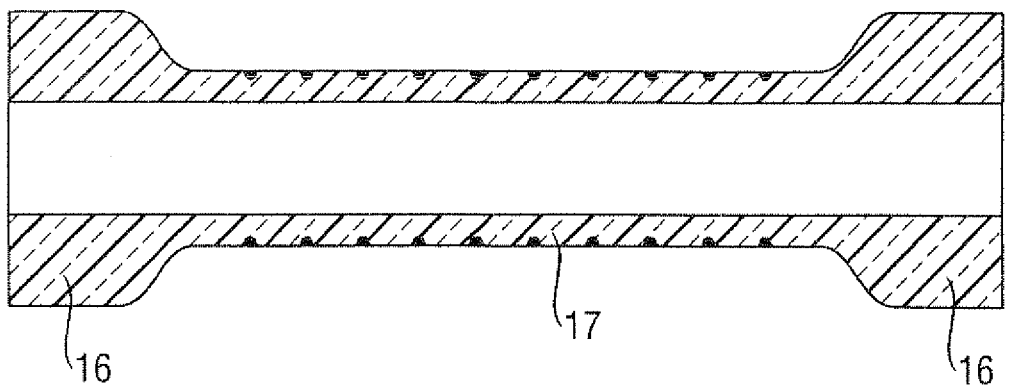
Figure 17:
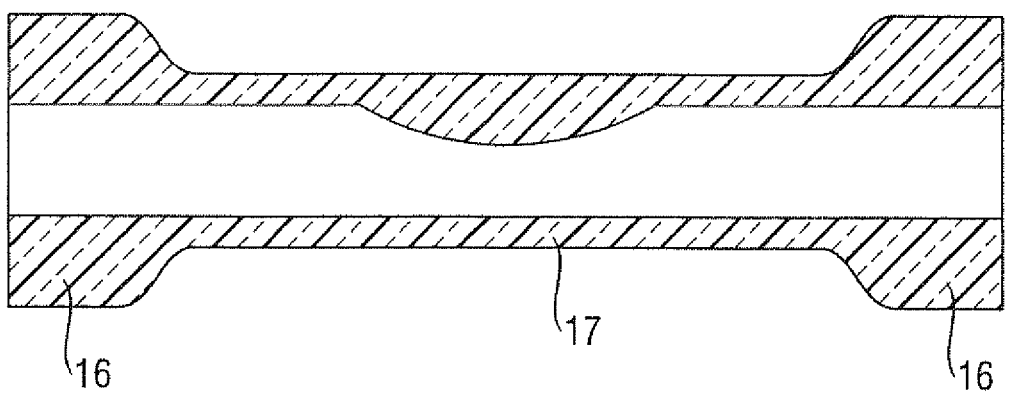
Figure 18:
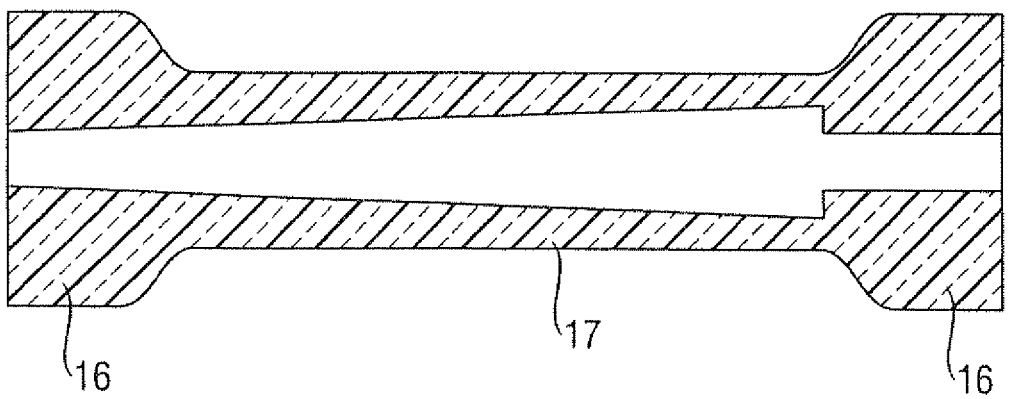
Figure 19:
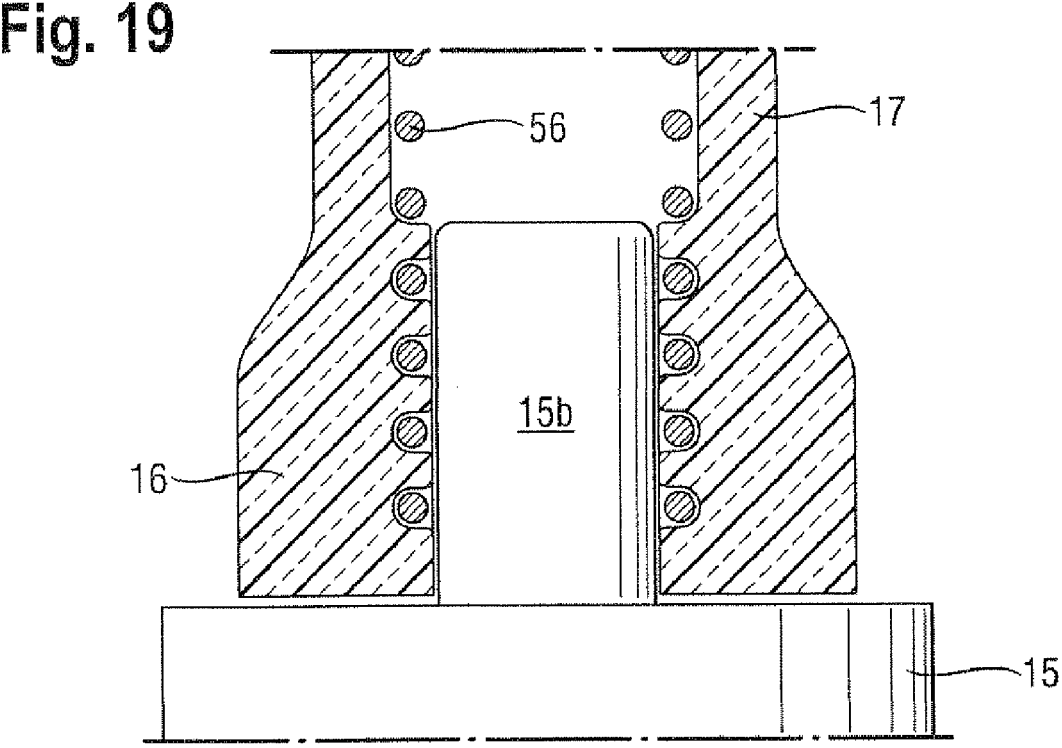
Figure 20:
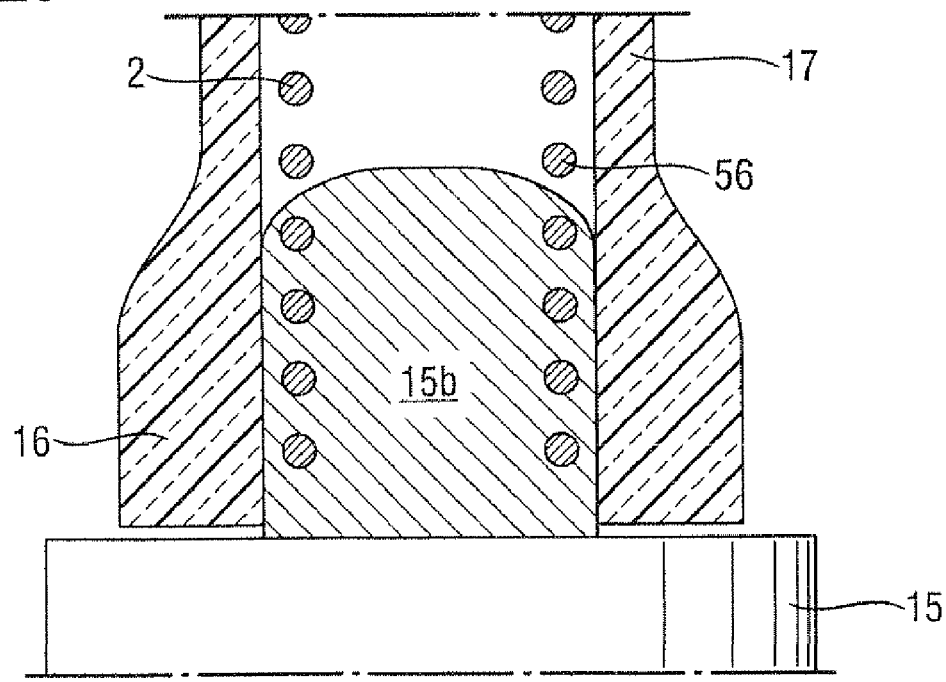
Figure 21:
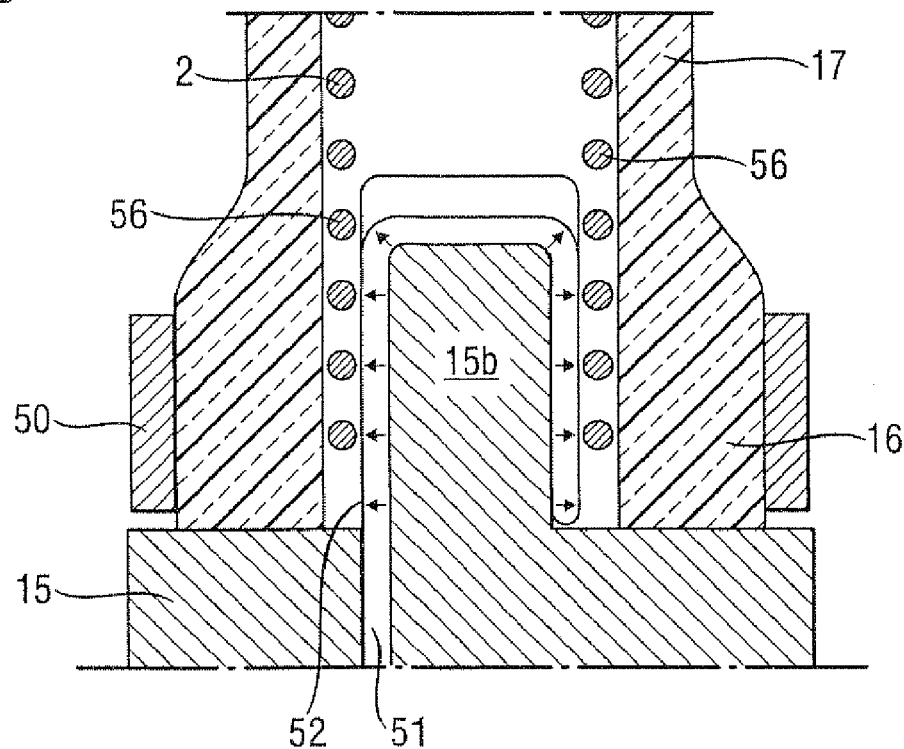
Figure 22:
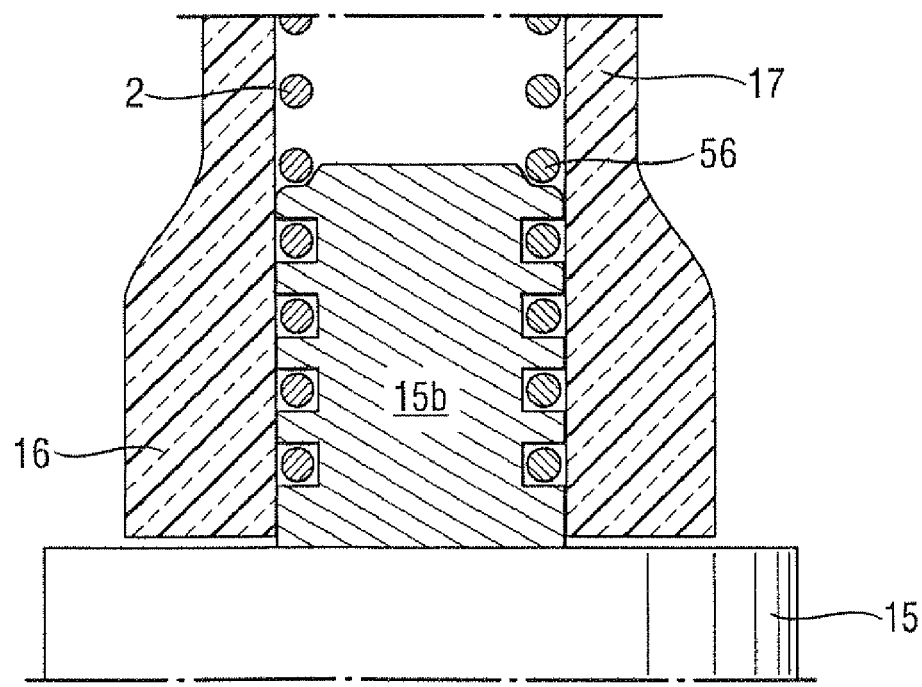
Figure 23:
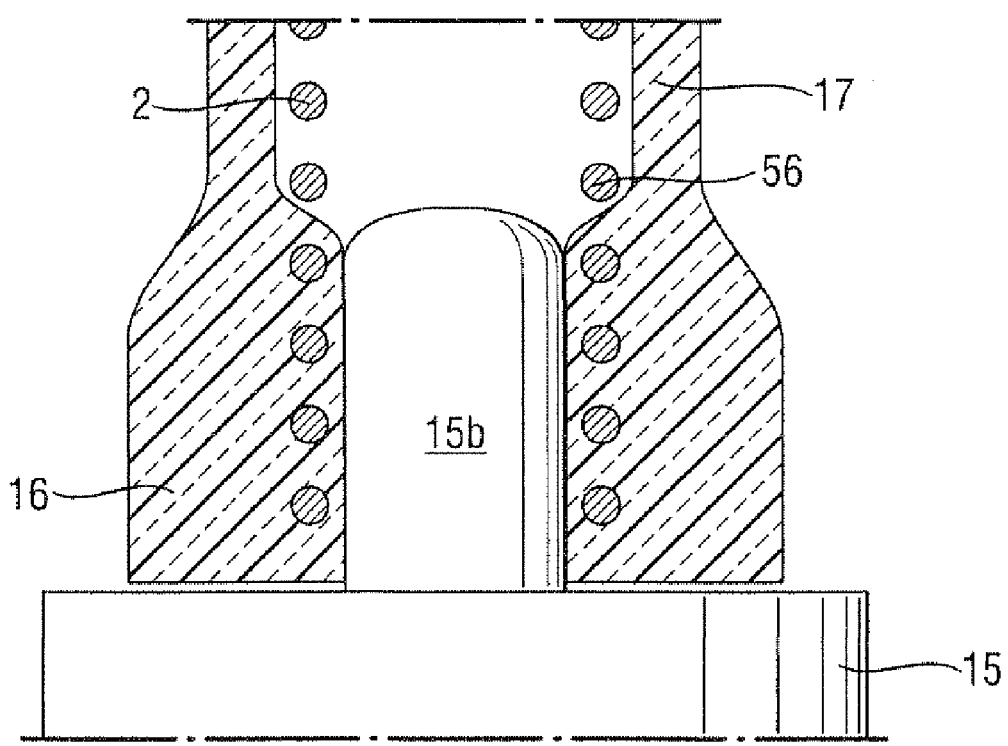

The disclosure is now further explained with reference to the drawing which shows in:

FIG. 1: schematically in cross section an embodiment of a holder according to the invention;

FIG. 2: schematically in cross section an embodiment of a holder according to the invention, holding a tubular implant structure;

FIG. 3: schematically in cross section an embodiment of a holder according to the invention:

FIG. 4A: schematically in cross section an embodiment of a holder according to the invention;

FIG. 4B: schematically a top view of the embodiment of a holder according to the invention as shown in cross section in FIG. 4A;

FIG. 5: schematically in top view an embodiment of a holder according to the invention;

FIG. 6: schematically an embodiment of a holder according to the invention associated with a fatigue test system;

FIG. 7: schematically an embodiment of a holder according to the invention associated with parts of a fixture assembly;

FIG. 8: the parts shown in FIG. 7 as assembled together,

FIG. 9: one of the parts shown in FIG. 7 as seen when viewing in the direction of arrow A;

FIG. 10: a part of a fatigue test system in which an embodiment of a holder according to the invention may be employed;

FIG. 11: the part shown in FIG. 10 as seen when viewing in the direction of arrow B;

FIG. 12: parts of a fatigue test system in which a holder according to the invention may be employed;

FIG. 13: schematically in more detail a part of a fatigue test system in which an embodiment of a holder according to the invention may be employed;

FIG. 14A-14H: a part of an embodiment of a holder according to the invention as used in various steps of using that embodiment;

FIG. 15: schematically in cross section an embodiment of a holder according to the invention;

FIG. 16: schematically in cross section an embodiment of a holder according to the invention;

FIG. 17: schematically in cross section an embodiment of a holder according to the invention;

FIG. 18: schematically in cross section an embodiment of a holder according to the invention;

FIG. 19: schematically in cross section a part of an embodiment of a holder according to the invention;

FIG. 20: schematically in cross section a part of an embodiment of a holder according to the invention;

FIG. 21: schematically in cross section a part of an embodiment of a holder according to the invention;

FIG. 22: schematically in cross section a part of an embodiment of a holder according to the invention;

FIG. 23: schematically in cross section a part of an embodiment of a holder according to the invention.

In the drawing, like parts have like references.

DETAILED DESCRIPTION OF EMBODIMENTS OF THE INVENTION

FIG. 1 shows schematically in cross section an embodiment of a holder according to the invention. Depicted is an implant holder 101 which is substantially flexible and which is suitable for holding a substantially tubular implant structure (not shown) during fatigue testing of that implant structure. Within the context of this specification is the word "flexible" meant to encompass not only bendable but also stretchable. The implant holder 101 has a substantially elongate cavity 102 for occupation by the tubular implant structure. The holder comprises a cavity-surrounding part 3 which extends from at least a first longitudinal end 104 of the cavity 102 to at least a second longitudinal end 105 of the cavity 102. The cavity-surrounding part 103 has a stiffness which gradually changes from a relatively high stiffness adjacent each of the longitudinal ends 104, 105 of the cavity 102 to a relatively low stiffness adjacent a middle portion which is situated between the two longitudinal ends 104, 105 of the cavity 102. The middle portion of the cavity 102 is indicated by the position of the letter M.

In the exemplary embodiment shown in FIG. 1, the cavity-surrounding part 103 comprises adjacent each of the longitudinal ends 104, 105 more material relative to the amount of material adjacent the middle portion. The portion of the cavity-surrounding part 103 that has a relatively high stiffness is indicated by the letters HS. The portion of the cavity-surrounding part 103 that has a relatively low stiffness is indicated by the letters LS.

The embodiment shown in FIG. 1 has obtained the gradual change in stiffness of the cavity-surrounding 103 by providing the cavity-surrounding part 103 adjacent each of the longitudinal ends 104, 105 with more material relative to the amount of material adjacent the middle portion M. The embodiment shown in FIG. 1 has rotational symmetry with respect to axis 107, as all other examples shown in this specification unless described otherwise.

FIG. 2 shows schematically in cross section an embodiment of a holder according to the invention, whilst holding a tubular implant structure 2. The longitudinal ends 104, 105 join in this embodiment another cavity, indicated by the letters OC. This other cavity OC may allow for connecting up with a controllably moveable part of a fatigue test system. In that case, the controllably moveable part is at a relatively long distance from the ends of the tubular implant structure. Consequently, the fixing of the implant holder 101 to these controllably moveable parts of the fatigue test system have itself no direct influence on ends of the tubular implant structure 2, both before and during fatigue testing.

FIG. 3 shows schematically in cross section an embodiment of a holder according to the invention, wherein the cavity-surrounding part 103 is adjacent each of the longitudinal ends 104, 105 made of a material having a high stiffness relative to the stiffness of the material of which the cavity-surrounding part 103 is made, adjacent the middle portion M. As shown in FIG. 3 this embodiment may have a laminate structure. A first material 111 may be employed for forming the cavity-surrounding part 103. This first material 111 may be employed from adjacent one of the longitudinal ends 104 to adjacent the other longitudinal end 105 of the cavity 102. A second material 112 may be applied adjacent each of the longitudinal ends 104, 105 of the cavity 102. The second material 112 will in this example be stiffer as compared to the first material 111. Along the axial direction of the implant holder 101 may the relative amounts of the materials 111 and 112 change gradually so that the stiffness of the cavity-surrounding part 103 will change gradually from a relatively high stiffness adjacent each of the longitudinal ends of the cavity to a relatively low stiffness adjacent the middle portion of the cavity 102.

It will be clear to a skilled person that although FIG. 3 shows a laminate structure of least two different materials, it is also possible to apply, say, a single polymer having a different degree of crystallinity adjacent the longitudinal ends 104, 105 as compared to the degree of crystallinity adjacent the middle portion M of the cavity 102. The crystallinity can also gradually change over a distance, so that also the stiffness gradually changes over that distance.

FIG. 4A shows in cross section an embodiment of a holder according to the invention, wherein the cavity-surrounding part 103 comprises a stiffness enhancing reinforcement structure 113 which is arranged to enhance the stiffness adjacent each of the longitudinal ends 104, 105 relative to the stiffness adjacent the middle portion M. The stiffness enhancing reinforcement structure 113 may comprise various windings 114. Although the windings 114 are in FIG. 4A as well as in FIG. 4B which is basically a top view of the embodiment shown in FIG. 4A, shown to be aligned in a strictly transverse direction, in reality the windings may all be part of a helix which could be incorporated in a matrix material 115, but which could also be applied at the outside of a tubular material 115, as shown in FIG. 5.

In FIGS. 4A, 4B and 5 is shown that the reinforcement structure may comprise adjacent each of the longitudinal ends 104, 105 more windings 114 relative to the number of windings 114 adjacent the middle portion M. However, although not shown, it will be understood that the reinforcement structure 114 may additionally, or alternatively, comprise adjacent each of the longitudinal ends 104, 105 thicker windings relative to the thickness of the windings 114 adjacent the middle portion M. There is an endless number of possibilities for providing an implant holder in accordance with the present invention. The skilled person will be able to identify existing tubular structures and to adapt these existing tubular structures such that the tubular structure becomes suitable for holding a substantially tubular implant structure during fatigue testing of the implant structure, in accordance with the present invention. It is, for instance, possible to remove from a relatively thick tubular structure an annular-shaped outer part of the structure so that a thinner cavity-surrounding part is formed around a middle portion of a the cavity defined by the tubular structure.

An implant holder according to the invention is not limited to the embodiment shown and discussed above. Many variations are possible. The cavity 102 may be substantially cylindrical, to conveniently hold a cylindrical tubular implant structure, or for instance be conical, to conveniently hold a conically shaped tubular implant structure.

The tubular implant structure may have the shape of an "hour glass". The holder may have a cavity particularly suitable for occupation by such an implant shape, for instance by providing a fitting cavity.

It is also possible that an implant holder according to the invention is a multiple part holder having at least two segments which in use neighbour each other in an axial direction. It is even not inconceivable to provide a implant holder which has a telescopic arrangement of segments which neighbour each other in use in an axial direction, but are also at least partly arranged in a co-axial manner.

It will be clear that the stiffness adjacent the longitudinal ends is not necessarily equal. At one end of the cavity the holder may be stiffer than at the other end of the cavity.

Below, it is further outlined how an implant holder according to the invention may be associated with various other devices, assemblies or systems, to provide an implant holder which allows for an optimal way of fatigue testing various tubular implant structures.

FIG. 6 shows schematically an example of a fatigue test system 1 for repetitively deforming a substantially tubular implant structure 2.

Such implant structures are widely used in medical and veterinary applications. Normally, the structure is meant to provide, or help providing, a passage for a flow. The passage can be a new passage, or a passage which used to exist but had for one reason or another ceased to exist or ceased to function. A passage in a body is usually required to be somewhat flexible, adapting its shape whilst remaining functioning as a passage, when the body changes its position from one to another, for instance during walking, sports etc. Such a flexibility requires the implant structure to be expandable and contractable within a radial range and within an axial range. The ranges in which the structure may expand and contract may differ between the axial direction and the radial direction. Before implanting such a structure into a human or animal body, it is important to know how many deformations such a structure can undergo during movements of the body, before the structure shows a failure, for instance in the form of a crack or in the form of plastic deformation leading to a different shape of the structure. A tubular implant structure that is meant to provide a passage in a body, has at least a first and a second end 2A and 2B.

A system for testing fatigue phenomena, i.e. phenomena which may occur after a large number of deformations of such a structure, comprise at least a first and a second part 3, 4 which are controllably moveable relative to each other.

A system according to the invention further comprises a first and a second fixture assembly 5, 6 for fixing the first end 2A of the tubular implant structure 2 to the first part 3 of the system 1 and the second end 2B of the structure 2 to the second part 4 of the system 1. As a result of this the system is capable of controlling the position of each of the first and second end of the tubular implant structure. Within the context of this specification is the phrase "controlling the position of each of the first and second end of the tubular implant structure" understood to mean directly regulating those positions, avoiding the occurrence of interfering phenomena which otherwise would play a role between the controlled position and the position of which control is desired.

Before describing in more detail examples of fixture assemblies 5, 6, the working of a fatigue test system 1 as schematically shown in FIG. 6 is described. In this example, the first part 3 of the first and second parts 3, 4 which are controllably moveable relative to each other, is fixed to a base 7. In this embodiment, part 3 does thus not move at all in a vertical direction. Second part 4 is connected to a construction element 8 that is driveable in the direction shown by arrow L. The nature of the driving mechanism can, for instance, be hydraulical, mechanical, or of any other suitable driving technology. The driving mechanism (not shown in detail) for linear movement of construction element 8 may be situated at a position where in dashed lines schematically a possible driving mechanism 9 is shown. It may alternatively, or additionally, for instance, be at a position where in the drawing solid lines show schematically a mechanism 10. In that case, driving mechanism 10 is providing a linear movement of construction element 8 in the direction of arrow L by moving up and down along guiders 11a and 11b. However, it is also possible that construction element L is moving up and down relative to driving mechanism 10. In that case, construction element 8 may be moving up and down as driven by a driving mechanism schematically shown by the dashed lines and referred to by 9. In the latter case, construction element 8 may be axially moving relative to a stationary and/or fixed axial bar 12. Elements 11a, 11b, earlier indicated as guiders, provide in a case where construction element 8 remains in rest relative to the position of the schematically shown mechanism 10, stiffness to the fatigue test system. The fatigue test system may also be provided with a bar 13 through which the elements 11a, 11b extend in an upward direction and through which the axis of construction element 8 may extend in an upward direction. This bar 13 may also provide stiffness to the fatigue test system.

As shown in the example of FIG. 6, two tubular implant structures may be tested simultaneously. It is possible that an array of implant structures 2 is situated along a direction perpendicular to the plane of the drawing. In such an arrangement, a very large number of tubular implant structures 2 could be subjected to identical repetitive deformation, which allows for improved statistics of the test results, and/or a fair comparison of the behaviour of the different tubular implant structures 2 which are subjected to identical repetitive deformations in a test wherein different tubular implant structures 2 are simultaneously tested. The system as discussed so far is arranged for moving the controllably moveable parts 3,4 relatively to and from each other along a predetermined line. For simply testing axial compression and/or axial elongation this predetermined line coincides with each axis of the tubular implant structures 2 fixed to the system 1.

Still with reference to FIG. 6, it is also possible that the second parts 4 of the fatigue test system 1 are rotatable, in a direction shown by arrow R, around an axis which coincides with the axis of the tubular implant structure that is fixed to that part 4 of the system 1. As the fixture assemblies 5 are fixed to respective parts 4 of the system 1, and the parts 3 are each non-rotatably fixed to base 7, the system is thus arranged for rotating the fixture assemblies 5, 6 relative to each other.

It will be clear that the fatigue test system as schematically shown in FIG. 6 is capable of subjecting the tubular implant structures 2 to a deformation that follows from axial compression or elongation and optionally combined with torsion. A fatigue test system that is capable of carrying out such tasks of controlling the positions of each of the parts 3,4 is known in the art and commercially available from manufacturers such as Zwick, Enduratech, Instron and MTS.

With regard to the fixture assemblies, it is pointed out that each fixture assembly may be capable of applying as a mechanism for fixing a form-fit mechanism and/or force-fit mechanism. An example of the latter will be discussed at this point of the specification. Other examples of the proposed mechanisms are later described.

In the embodiment shown in FIG. 6 each fixture assembly 5, 6 comprises a clamp. With reference also to FIGS. 2, 3 and 4, the fixture assemblies 5, 6 each comprise an insertable holder 15 for inserting fittingly into one of the ends 2A, 2B of the tubular implant structure 2. The insertable holder 15 has an insertable end 15A for inserting fittingly into one of the ends 2A, 2B the tubular implant structure 2. The insertable holder 15 also has a fixable end 15B for fixing with one of the parts 3, 4 which are controllably moveable relative to each other. The insertable end 15A is preferably a bit rounded off so that insertion is unlikely to result in internally damaging the tubular implant structure 2. The particulars of the fixable end 15B will later be discussed further below.

Each of the fixture assemblies 5, 6 further comprises at least one tightenable embracing holder for tightly embracing that one end of the tubular implant structure 2 that has the insertable holder 15 inserted in it.

The embracing holder may comprise a substantially ring-shaped elastic holder 16. In the embodiment shown in the drawing the ring-shaped elastic holder 16 is part of a substantially flexible implant holder, in this and the following examples depicted as tube 17, which has preferably a length that is In the examples shown in the drawing, the embracing holder further comprises a substantially ring-shaped holder 18 which fits around the elastic holder 16 and which is provided with a tightening mechanism. An example is shown in FIG. 9. The holder 18 comprises two metal strips 48, 50 which have overlapping parts 48A, 50A through which a screw 52 extends. The strip 50 comprises further a longer part 50B that is curled up in itself. Strip 48 further comprises a part 48B that is somewhat stiffer than part 50B. Part 48B partly embraces the curled-up part 50B. The tightening mechanism works as follows: When the screw is screwed towards the curled-up part 50B, that part is forced to curl up even further so that the inner diameter of the curled-up part becomes smaller. The part 48B prevents that the curled-up part is pushed away by the advancing screw and facilitates the curling up of part 50B. As shown, the curling up part 50B may be forked and be provided with a relatively stiff curved plate-like part 49. The end of screw 52 may also be provided with a plate-like element 51 having a convex surface facing the curved plate-like part 49. When the screw 52 advances, the interaction between the touching curved plate-like part 49 and the convex surface of element 51 facilitate the forcement of the curling up of part 50B without crushing that part 50B.

Clearly, the diameter of the curled-up part 50B can be controlled over a wide range. The mechanical properties of part 50 are such that upon screwing screw 52 outwards, the diameter of curled-up part 50B increases.

Many variations of the tightening mechanism are possible. Such ring-shaped holders 18 with a tightening mechanism are well known in the art and commercially available at most hardware stores. It may apply, as shown, that the tightenable embracing holder is itself an assembly of a ring-shaped elastic holder and a ring-shaped holder provided with a tightening mechanism. However, it is, of course, also possible that the tightenable embracing holder is one device, for instance comprising an embracing holder with a tightening mechanism wherein the inside of the embracing holder comprises a substantially ring-shaped elastic part.

With particular reference to FIGS. 7, 8 and 9, in the following explanation is given as to how the fixture assemblies 5, 6 are fixed to the respective ends 2A, 2B of the tubular implant structure 2. In this explanation it is assumed that the tubular implant structure 2 has already been embraced by the inner ring-shaped elastic holder 16, which is in the exemplary explanation assumed to be an integral part of the tube 17. The way in which the tubular implant structure tube may have been inserted into the tube 17 will be explained further on in this specification. It will be clear though that instead of tube 17 also two separate elastic holders may be employed.

Into each end 2A, 2B of the tubular implant structure 2 is the insertable part 15A of the insertable holder 15 inserted while the tubular implant structure 2 itself is situated within tube 17. The tightenable embracing holder 18 is provided around each end of the tube which comprises at each end a ring-shaped elastic holder 16 as part of the tube 17. The embracing holder 18 as shown in FIG. 9, has the capability of having a large diameter to facilitate easy placement of the embracing holder around the fixable end 15B of the insertable holder 15 and around the ring-shaped elastic holder 16. When the tightly embracing holder is rightly positioned at one of the ends 2A, 2B of the tubular implant structure, the tightening mechanism is employed to tighten the embracing holder, so that the ring-shaped elastic holder 16 is being squeezed tightly against the respective end 2A, 2B of the tubular implant structure 2. The elasticity of the ring-shaped elastic holder 16 ensures that it is the ring-shaped elastic holder itself which is being deformed when being squeezed rather than the respective end 2A, 2B of the tubular implant structure 2. The ends 2A, 2B of the tubular implant structure 2 cannot be crushed as the insertable part 15A of the insertable holder provides internal support to the ends 2A, 2B of the tubular implant structure 2. The elastic material of the elastic holder 16 distributes the radial inward load applied by the tightenable holder, homogeneously, avoiding the occurrence of local high stresses. The elastic holder 16 will press against the insertable part 15A of the insertable holder, in the case of a stent as test member, through "apertures" available between the struts of the stent, and "lock" as such an end of the stent between the elastic holder 16 and the insertable part 15A. Hence, the fixture assembly is tightly fixable to the respective end 2A, 2B of the tubular implant structure 2, whilst minimizing local plastic deformation or any other alteration of the tubular implant structure 2. FIG. 3 shows the end result of this assembling process.

FIGS. 10, 11 and 12 show in more detail the parts of the system which are involved with the fixation of the fixture assemblies 5, 6 with respectively the systems first and second parts 3, 4 which are controllably moveable relative to each other. FIGS. 10 and 11 show such a part from different angles. FIG. 10 shows the part as seen in FIG. 11 when viewed in the direction of arrow C. FIG. 11 shows the part as shown in FIG. 10 when viewing in the direction of arrow B. FIG. 12 shows how these parts 4,5 can be connected such that the fixture assembly, i.e. the fixable part 15B thereof, is fixed with one of the parts 3,4 which are controllably moveable relative to each other. It will be understood that for a complete fixation a locking pin can be entered through hole 18A and 18B when these are aligned. Many other possibilities of fixation of the fixable end 15B with one of the parts 3, 4 are possible. FIG. 10-12 provide merely a construction that has proved to work very well.

An embodiment of a system according to the invention may be arranged so that the fixture assemblies will in use be hingeable within a predetermined imaginary plane when the fixture assemblies are relatively moved, to and from each other. FIG. 13 provides an example of a part of a hingeable fixture assembly. The insertable holder is in this example hingeably designed. The fixable end 15B is hingeably connected to the insertable end 15A of the insertable holder. A set screw 20 can set the initial angle formed by the axis of the fixable end 15B and the axis of the insertable end 15A, so that when the part 4 moves in the direction of arrow D relative to its not shown counterpart 3, the direction of bending is predetermined. It will be understood that the counterpart 3 will have to be provided with a similarly oriented hingeably fixture assembly if the tubular implant structure 2 were to be subjected to a bending movement within a straight imaginary plane.

In more general terms, a method of connecting the substantially tubular implant structure 2 to the first and second controllably moveable parts 3,4 of the fatigue system 1 comprises form-fitting and/or force-fitting the first end 2A to the first controllably moveable part 3 and the second end 2B to the second controllably moveable part 4. Towards the end of this specification a number of more detailed embodiments of this method will be shown and discussed. Right now, one embodiment of such a method is described in more detail.

Reference is made to the FIG. 7-12. The substantially ring-shaped elastic holders 16 are put around each of the first and second end 2A, 2B. Into each end of the tubular implant structure 2 is the insertable part 15A of one of the insertable holders 15 inserted. The tightenable embracing holder 18 is provided tightly around each substantially ring-shaped elastic holder 16 when that holder is around an end 2A, 2B of the tubular structure 2. Finally, of each insertable holder 15 is a fixable part 15A connected to one of the controllably moveable parts 3, 4 of the fatigue testing system 1.

As outlined above the two substantially ring-shaped elastic holders 16 can be provided as a tube of an elastically deformable material.

In the following it will be described how the tubular implant structure 2 can be inserted into a tube 17. In this case, the tubular implant structure 2 is inserted into the tube 17 whilst the structure 2 is in a condition wherein the outer diameter of the tubular implant structure 2 is at most equal to the inner diameter of the tube 17. The tubular implant structure 2 is then conditioned into a radially expanded condition wherein the outer diameter of the tubular implant structure 2 is at least equal to the inner diameter of the tube 17. Applying the method as such results in a situation wherein the tubular implant structure 2 and the tube 17 are both relative to each other axially relaxed.

However, it may be advantageous to have the tubular implant structure 2 axially compressed relative to the tube 17. In that case additional steps need to be applied. The steps involve conditioning the tube 17 into an elastically elongated condition before inserting tubular structure 2 into the tube 17. Further, the tightenable embracing holder 18 is provided around each end of the tube 17 whilst tube 17 is in the elastically elongated condition and the tubular implant structure 2 is in the tube 17 in the radially expanded condition. Finally, the tube 17, having the tubular implant structure 2 inserted into it, having the insertable part 15B of the insertable holder 15 into each end of the tubular implant structure 2, and being provided with the tightenable embracing holder 18 around each end of the tube 17 is relaxed back into an elongated condition.

For the application of in particular the latter method dedicated tools may facilitate reproducibility and convenience. With reference to FIG. 14A-14G it is pointed out that an embodiment of a system according to the invention may for this purpose be provided with a preparation assembly 30 which is schematically shown as seen from above. The preparation assembly 30 comprises a guider 31 and two holders 32A and 32B which are fixable to the guider 31 and moveable to and from each other from the guider 31. Each of the holders 32A, 32B define a recess 33A, 33B for holding one end 16 of the tube 17. Further on below the tube 17 will be discussed in more detail. At this stage it is merely indicated that the tube is preferably of an elastically deformable material and that preferably at least part of the tube may be transparent.

Figure 14A:
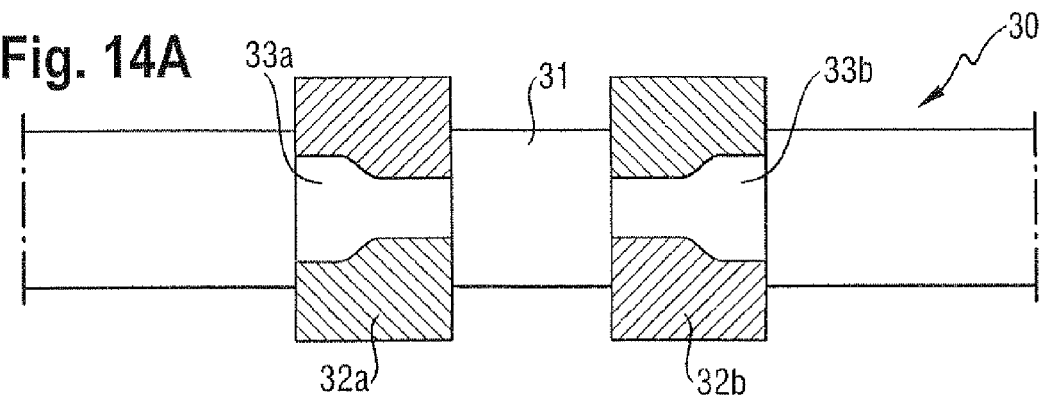
Figure 14B:
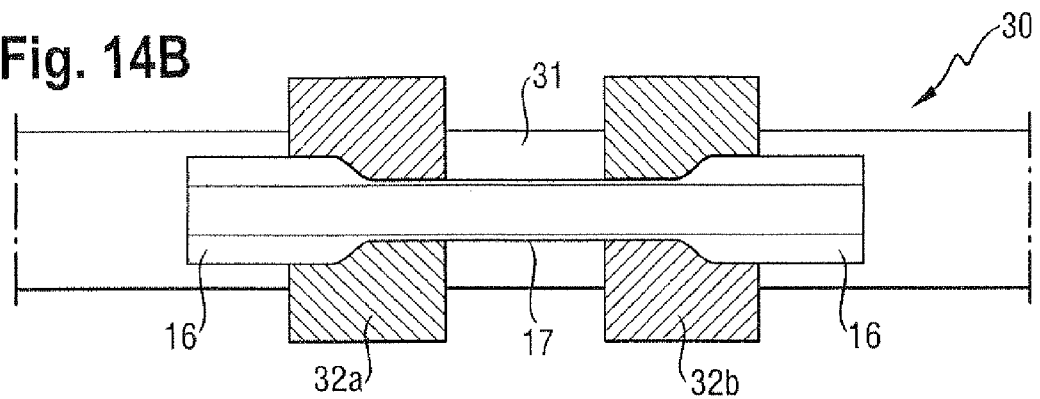
Figure 14C:
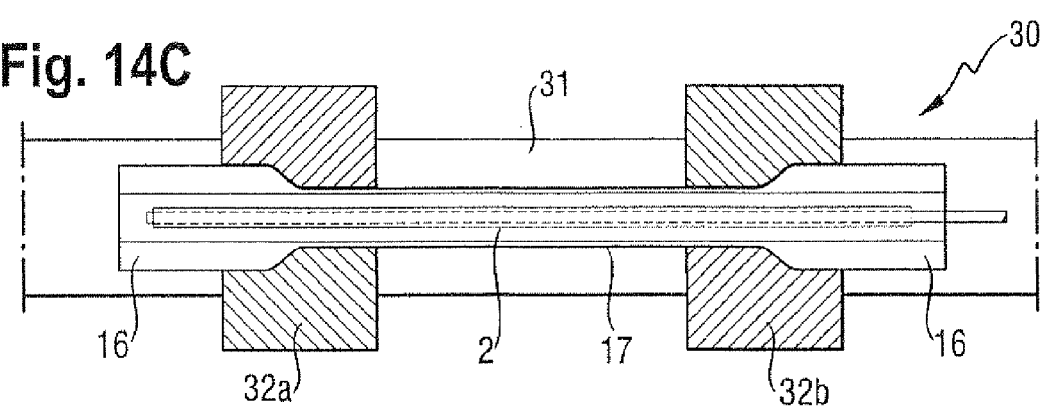

As shown in FIG. 14B the tube 17 can be placed such that each part 16 of the tube 17 is fittingly situated in respectively recess 33A and recess 33B of, respectively, the holders 32A and 32B. The holders 32A and 32B can then be moved relative to each other along the rail such that the distance between the holders 32A and 32B becomes larger. As a result of this, the tube 17 will be elongated as shown in FIG. 14C. A skilled reader will appreciate that it is the middle portion of the tube 17, between the ends 16, that will be elongated, rather than the elastic holders 16 themselves. When the tube 17 is the elongated condition, the tubular implant structure 2 is inserted into the tube 17. During this insertion is the tubular implant structure 2 in a condition wherein the outer diameter of the tubular implant structure 2 is at most equal to the inner diameter of the tube 17 when in elongated condition. Ideally the outer diameter of the tubular implant structure 2 is a little smaller than the outer diameter of the tube 17 when in elongated condition.

FIG. 14C shows also the insertion of the tubular implant structure 2. A device similar or identical to a catheter is employed for the insertion, in a way well known to those skilled in the art. It will be clear that the use of a transparent tube facilitates this step.

In a next step the tubular implant structure 2 is conditioned into a radially expanded condition wherein the outer diameter of the tubular implant structure 2 is at least equal to the inner diameter of the tubular implant structure 2 when in elongated condition. The expansion of such a tubular implant structure 2 can take place by, for instance, the use of a balloon kept within the radially compressed tubular implant structure 2 at the end of the catheter and blowing this balloon up so that an internal radially outward pressure is applied to the tubular implant structure 2. However, it is also possible that the tubular implant structure 2 is a so-called self-expander, and that during insertion of the tubular implant structure 2 in the radially compressed condition a so-called retractable sheath covers the tubular implant structure 2. Upon retraction of the retractable sheath when the tubular implant structure 2 has been inserted into tube 17, such a self-expander will radially expand into a radially expanded condition. Finally, there is a possibility, that a tubular implant structure radially expands upon a change in the temperature of the structure. This applies to a so-called Nitinol stent, as well known in the art.

Figure 14D:
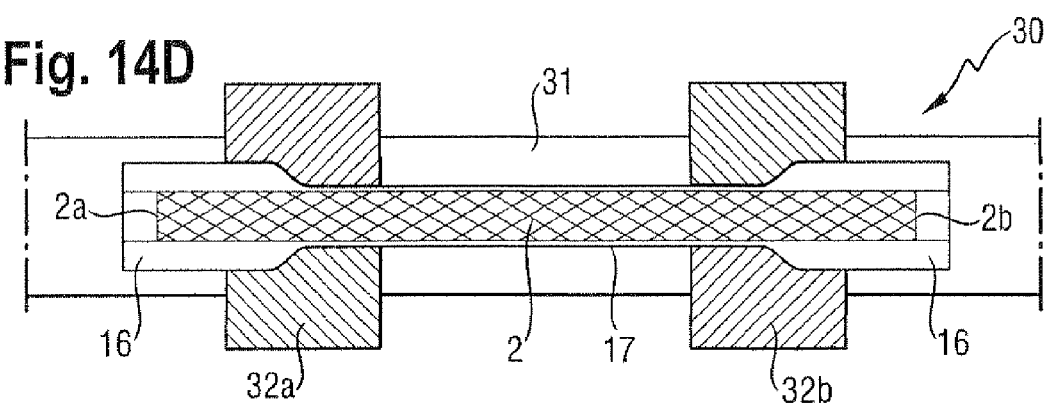
Figure 14E:
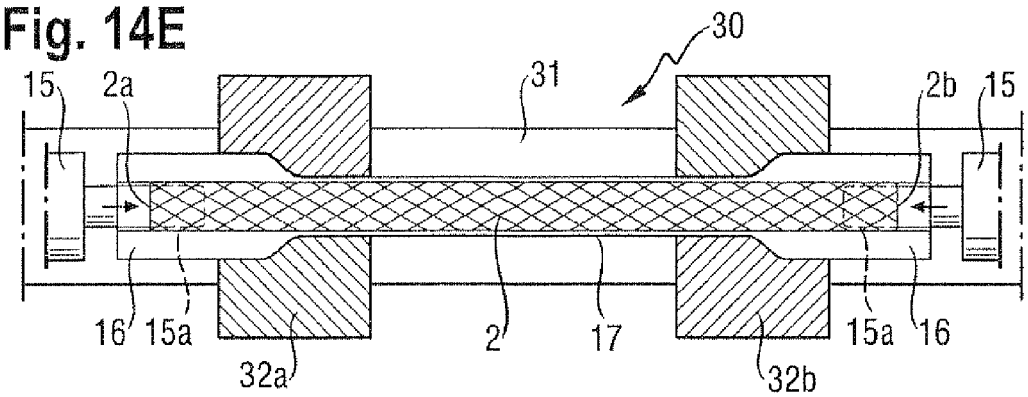

FIG. 14D shows the situation after insertion of the tubular implant structure 2 and conditioning this structure into the radially expanded condition. FIG. 14E shows a next step involving insertion into each end 2A, 2B of the tubular implant structure 2 an insertable part 15a of an insertable holder 15.

Figure 14F:
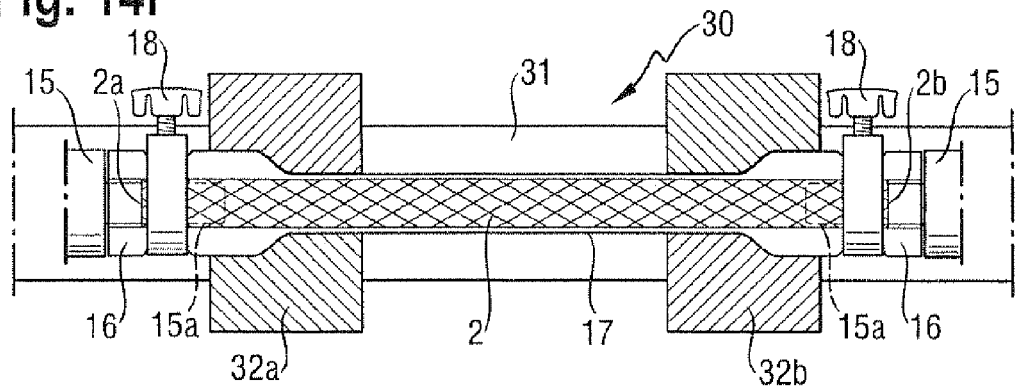

In the next step a substantially ring-shaped holder 18 with a tightening mechanism as shown in FIG. 9 is tightly placed round each end 16 of the tube 17. In a method of which an exemplary embodiment is shown in FIG. 14A-14H, the tube is during this step still in the elastically elongated condition and the tubular implant structure 2 is in the tube 17 in the radially expanded condition. The result of this step is shown in FIG. 14F.

Figure 14G:
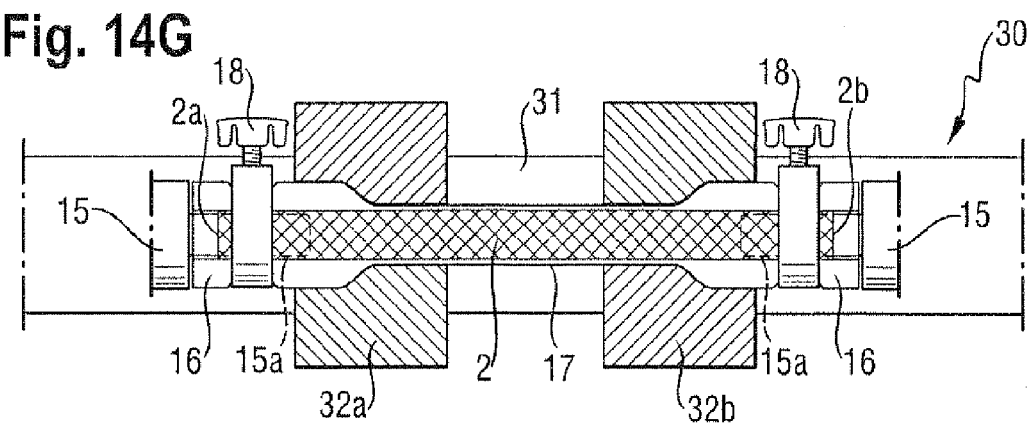
Figure 14H:
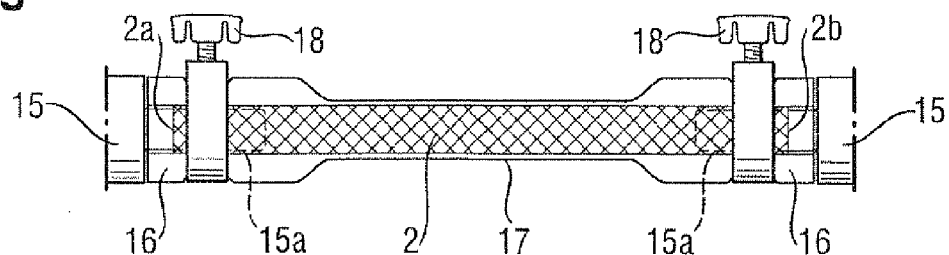

In a next step, tube 17 is relaxed from its axially elongated condition back towards its natural, unstrained, condition. This is done, for instance, by moving the holders 32A,32B along the guider 31 relative to each other. This step is schematically shown in FIG. 14G. However, the tube may not end up in a fully relaxed position as the stent in the tube may cause the tube to be, for instance, somewhat blocked in its attempt to obtain a fully relaxed condition.

As a result of the relative relaxation of tube 17 and the fixation of the tubular implant structure 2 at its ends 2A, 2B to the ends 16 of tube 17, will the tubular implant structure 2 be conditioned into an axially compressed condition. The tube 17, having the tubular implant structure 2 inserted in it, having the insertable parts 15A of insertable holders 15 into each end 2A, 2B of the tubular implant structure 2, and being provided with the tightly embracing holders 18 around each end 16 of the tube 17, is in FIG. 14H as shown back into its non-elongated condition. The fixable ends 15B (not shown in FIGS. 14A-14H) can now be fixed to the parts 3, 4 of the fatigue test system, for instance, in a way as described earlier.

It will be clear that when the tubular implant structure 2 is not required to be in the axially compressed condition when fixed to the fixture assemblies 5,6, all the steps shown in FIG. 14A-14H apply, apart from the steps which involve conditioning the tube 17 into the elastically elongated condition before insertion of the tubular implant structure 2 into the tube 17 and apart from the step involving the relaxing of the tube 17 back into the non-elongated condition.

Tube 17 will now be discussed with reference to FIGS. 15, 16, 17 and 18. It has already been indicated that a tube 17 is of an elastic material. The tube 17 may also be of an elastomeric material or various combinations of natural tissues (e.g., porcine vein or porcine artery) and elastomeric (e.g., silicone, polyurethane, PET, PTFE, to name a few) material. The tube 17 is preferably of a material which mimics mechanical properties of mammalian vessel or tissue. The tube is preferably of such a material that at least a part of the tube 17 is transparent. Such transparency would also facilitate visually monitoring deformation of the tubular implant structure when the tube is being subjected to repetitive deformation. It is possible that the tube 17 is provided with markings which allow for monitoring, for instance, the deformation of the tube itself relative to the deformation of the tubular implant structure 2. Such markings may be made of ink, but may also be, for instance, of a metal. Such markings 35 may also be formed by recesses or protrusions on the outer side of the tube 17.

As indicated above, the outer diameter of the tube 17 is adjacent end portion 16 of the tube 17 larger than the outer diameter of a portion that is situated in a middle portion of the tube 17. Although in the FIG. 15-18 the transition from the smaller outer diameter toward the larger outer diameter is shown to be somewhat angular, it is also possible that the tube is provided with very smooth and more rounded-off transitions.

Although in most embodiments the inner diameter of the tube 17 will be constant over the length of the tube 17, it is possible that the inner diameter of the tube 17 varies along the longitudinal direction of the tube 17. The examples shown in FIG. 15 may be useful for a tubular implant structure that is meant to be inserted at a position where a severe stenosis becomes part of the likely deformation of the implant structure when subjected to movements, it is also possible that a tube 17 is provided with a cavity to mimic situations where the stent is used in a situation where severe aneurysm is having an influence on the likely deformation of the implant structure. FIG. 17 shows an embodiment wherein the inner space of the tube 17 is tapered, useful for a situation wherein only a part of the tubular implant structure is likely to be held tightly by, for instance, the inner wall of a vessel or in a situation where the vessel itself is tapered, such as the tapered carotid vessel. It should be noted that the examples discussed above and shown in FIG. 15-17 may or may not have rotational symmetry.

FIG. 18 shows an embodiment of a tube 17 having a bifurcation, useful for testing tubular implant structures having at least three ends. It will be clear that for testing such a tubular implant structure, the entire fatigue test system should be adapted, in a way as will also be clear for those skilled in the art.

A suitable material for a tube 17 is a silicon rubber, for instance, siloprene 2050 as available from Bayer. Any other material that mimics vessel properties, such as the Poisson ratio, would in principle be worth considering.

As mentioned above, many types of predetermined deformations can be imposed onto a tubular implant structure as held by the fixture assemblies 5, 6 as described above in an embodiment of a fatigue test system according to the invention.

It is possible to subject the tubular implant structure to, for instance, bending, elongation and bending, compression and bending, compression and elongating, torsion, torsion and elongation, torsion and compression, torsion and bending, etc. During a torsion test it may be preferable to have the tube 17 slightly stretched, i.e. elongated, while the tubular implant structure is in a relaxed condition. Then, the earlier described method for conditioning the tubular structure in an axially compressed state, can be employed. This can obviously also be achieved using the preparation assembly as shown in FIG. 14A-14H.

A main function of the tube is the prevention of kinking of the tubular implant structure and the possibility to hold the structure in an axially compressed condition relative to the tube. As a result of this the fatigue test can be carried out while the structure is overall in a "neutral", i.e. axially relaxed condition but held tight by the elongated tube. Of importance is also the facility to provide a test-surrounding to the tubular structure, not unsimilar to the circumstances to which the structure is subjected when inserted intraluminally in a body. The tube can provide such a test-surrounding.

As indicated above, more embodiments of force-fitting and/or form-fitting the ends 2A, 2B of the tubular implant structure 2 to the controllably moveable parts 3, 4 are conceivable. In the FIGS. 19-23 the controllably moveable parts 3, 4 themselves are not shown. Visible though is the insertable part 15B of the insertable holder 15. The part 15A for connecting up that insertable part 15 to the controllably moveable parts 3, 4 is shown in, for instance, FIG. 12 and FIG. 13.

So far, the force-fitting embodiment shown above, applied a radially inward clamping force provided by the tightenable embracing holder 18. FIG. 19 shows an embodiment wherein the clamping force is applied from within the end 2A, 2B of the tubular implant structure 2 radially outward so that the ends 2A, 2B of the tubular implant structure tube is pressed with its outer surface against the inner cylindrical surface of the elastic holder 16, in this example being an end of tube 17. For expanding the inner diameter of the insertable part 15B of the insertable holder 15 is a variety of mechanisms available, all well-known in the art. One application as shown comprises the introduction of a fluid under high pressure in a channel 51 that has an elastic outer wall 52. However, it is also possible to axially compress a rubber O-ring by tightening, for instance, a screw, as well-known in the art. Around the outer end of the tube 17, i.e. around the elastic holder 16 may a relatively stiff ring 50 be applied to ensure that the elastic holder 16 is not itself completely pushed radially outwards but does provide the necessary reaction force so that the clamping will be effective.

With reference to FIGS. 20-23, further embodiments of a form-fitted connection between the ends 2A, 2B of the tubular implant structure 2 and the insertable part of the fixture assembly is schematically shown and will now be further discussed. FIG. 18 shows an embodiment wherein the insertable part 15B of the insertable holder 15 is provided with recesses 54 for occupation of the end 2A, 2B of the tubular implant structure 2. The elastic holder 16, in this example an end of the tube 17, closes the recesses off so that the end of the tubular structure 2 is locked in, i.e. form-fittedly connected to the insertable holder 15 which is in itself connectable to the controllably moveable parts 3, 4 of the fatigue system 1. A ring 50 as shown and discussed in relation to FIG. 19 may equally be applied.

In the FIGS. 19-23 the tubular implant structure 2 is schematically shown by a multitude of cross sections of struts 56, as well-known in the stents. It will be clear that for force-fitting the tubular implant structure is not required to have apertures available between struts 56. However, for the embodiments using a form of form-fitting, such apertures come in very handy.

With regard to FIG. 21, it is pointed out that the recesses for occupation of the ends 2A, 2B of the tubular implant structure 2, may alternatively, or additionally, be provided in the elastic holder 16, as part of the tube 17.

Finally, FIGS. 22 and 23 show embodiments wherein the end of the tubular implant structure 2 is embedded in either the insertable part 15B of the insertable holder 15 (FIG. 22) or the elastic holder 16, in these examples being part of tube 17 (FIG. 23). It will be understood that such embedding requires more preparation, but such an application is not inconceivable, and workable for those skilled in the art.

It will be clear to the skilled reader that also a combination of form-fitting and force-fitting can be employed. It will further be clear that the relative stiffness of the materials of the insertable part 15B of the insertable holder 15 and the elastic holders 16 need to be chosen such that the selected way of fitting will be obtained. However, this is a routine matter for one skilled in the art.

It will also be clear that a fixture assembly may comprise an insertable holder for fitting tightly into one of the ends of the tubular implant structure, and one embracing holder for embracing that one end of the tubular implant structure that has the insertable holder inserted in it.

With reference again to FIG. 6, it is indicated that the fatigue test system may be provided with a monitoring device 40, as schematically drawn in dashed lines. Such a monitoring system may rely on a technology selected from, for instance, X-ray technology, infrared technology or visual technology. Although such a monitoring system is clearly situated for monitoring the tubular implant structure from outside that structure and even from outside tube 17, it is also possible that monitoring devices are also guided into the tube 17 and the tubular implant structure 2. In particular, visual inspection using a minute CCD camera capable of obtaining close shot images of the deformation of the tubular structure, is amongst the various possibilities.

It may also be possible that monitoring occurs by means of detection of crack formation using, for instance, technology such as impedance measurements, acoustic measurements, and electric potential measurements. A method of testing a substantially tubular implant structure as described above may further comprise testing a number of selected tubular implant structures out of a plurality of identical tubular implant structures. The behaviour of the selected tubular implant structures may be held as representative for each of the pluralities of the identical tubular implant structures.

It is pointed out that the method for holding the tubular implant structure in an axially compressed manner in and relative to the tube can also be applied to any other holder for holding a substantially tubular implant structure during fatigue testing. In that case, the implant holder is an axially and elastically elongatable implant holder having a substantially tubular shape. The method comprises in that case conditioning the holder into an elastically elongated condition before inserting the tubular implant structure into the holder. A further step comprises inserting into the holder the tubular implant structure. While the holder is in the elastically elongated condition and the implant structure has been inserted into the holder, each end of the tubular implant structure is fixed to the holder. Having the tubular implant structure fixed to it, the holder is relaxed back into a non-elongated or less elongated condition. The holder not necessarily has to be in one of the shapes described and discussed above.

It is possible that for application of this method also a preparation assembly is used for facilitating the fixing of the tubular implant structure in an axially compressed manner in and relative to the holder. As the implant holder has not necessarily the shape of a tube or implant holder as described above, also two holders of a preparation assembly have not necessarily the shape as shown in FIGS. 9A-9H. More in general, the two holders of the preparation assembly and the implant holder are designed such that each of the two holders of the preparation assembly can engage with the implant holder so that the implant holder is conditioned into an elastically elongatable condition when the two holders of the preparation assembly are moved relatively away from each other. It is for the skilled person a routine method to design the implant holder and the two holders of the preparation assembly such that this function can be achieved.

The invention is not limited to the embodiments described above. Many additional measures, or alternative measures, are possible.

To ensure that the temperature of all tubular structures tested are similar, the actual specimens may be held in a water tank during the testing. Instead of water, another fluid may be present, for instance saline or bile. It is further possible to let water flow through the tube 17 so that the tubular implant structures are subjected to deformation under circumstances as may be applicable when those structures are subjected to deformation in a body. All such variations are understood to fall within the framework of the invention as described in the appended claims.

It will further be clear that many combinations of different embodiments are possible. For instance, one of the fixture assemblies may be based on an embodiment as shown in FIG. 23, whereas the other one of the fixture assemblies may be based on an embodiment as shown in FIG. 13. Likewise it is possible to have a fixture assembly based on an embodiment as shown in FIG. 20 combined with a fixture assembly based on an embodiment as shown in FIG. 13 or, say FIG. 7).

It will also be clear that a fixture assembly may comprise an insertable holder for fitting tightly into one of the ends of the tubular implant structure; and one embracing holder for embracing that one end of the tubular implant structure that has the insertable holder inserted in it.

The following numbered paragraphs provide further disclosure of the present subject matter:

1. A medical prosthesis test system comprising:
   a base portion connected to a supporting framework, the base portion having a first fixture member;
   a structure that moves in at least two directions relative to the supporting framework, the structure having a second fixture member;
   a conduit having a first conduit end fixed to the first fixture member so that there is generally no relative movement of the first conduit end with respect to the first fixture member, the conduit having a second conduit end fixed to the second fixture member so that there is generally no relative movement of the second conduit end with respect to the second fixture member when the structure is moved in any one of the at least two directions.

2. The system of paragraph 1, further comprising a medical prosthesis having first and second prosthesis ends, the first prosthesis end being fixed to both the first conduit end and the first fixture member, and the second prosthesis end being fixed to both the second conduit end and the second fixture member.

3. The system of paragraph 1, wherein the conduit comprises a generally tubular elastomeric member having a first wall thickness proximate one of the first and second conduit ends, a second wall thickness proximate the other of the first and second conduit ends, and a third wall thickness at a location between the first and second conduit ends.

4. The system of paragraph 3, wherein the first wall thickness is greater than the second wall thickness and the third wall thickness.

5. The system of paragraph 3, wherein the first wall thickness is approximately equal to the second wall thickness.

6. A method of testing a medical prosthesis having a first prosthesis end and a second prosthesis end disposed along a longitudinal axis, the method comprising
   capturing the first prosthesis end between a first outer conduit end and a first inner conduit end to prevent relative movements;
   capturing the second prosthesis end between a second outer conduit end and a second inner conduit end to prevent relative movements, and
   moving the first prosthesis end relative to the second prosthesis end without relative movements of the first prosthesis end to the first outer and inner conduits and without movements of the second prosthesis end relative to the second outer and inner conduits.

7. The method of paragraph 6, wherein the moving comprises rotating one of the first and second prosthesis ends about an axis offset to the longitudinal axis.

8. The method of paragraph 7, wherein the moving comprises translating along the longitudinal axis one of the first and second prosthesis ends to and from the other of the first and second prosthesis ends.

9. The method of paragraph 8, wherein the moving comprises translating one of the first and second prosthesis ends along an axis generally orthogonal to the longitudinal axis.

All such variations are understood to fall within the framework of the invention as described in the appended claims.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention.

Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

The invention claimed is:

1. A substantially flexible implant holder for holding a substantially tubular implant structure during fatigue testing of the implant structure, the implant holder having a substantially elongate cavity for occupation by the tubular implant structure and a cavity-surrounding part which extends from at least a first longitudinal end of the cavity to at least a second longitudinal end of the cavity, the cavity-surrounding part having a stiffness which gradually changes from a relatively high stiffness adjacent each of the longitudinal ends of the cavity to a relatively low stiffness adjacent a middle portion which is situated between the two longitudinal ends of the cavity.

2. The implant holder according to claim 1, wherein the cavity-surrounding part comprises adjacent each of the longitudinal ends more material relative to the amount of material adjacent the middle portion.

3. The implant holder according to claim 1, wherein the cavity-surrounding part is adjacent each of the longitudinal ends at least partly made of a material having a high stiffness relative to the stiffness of the material of which the cavity surrounding part is made adjacent the middle portion.

4. The implant holder according to claim 1, wherein the cavity-surrounding part comprises a stiffness-enhancing reinforcement structure which is arranged to enhance the stiffness adjacent each of the longitudinal ends relative to the stiffness adjacent the middle portion.

5. The implant holder according to claim 4, wherein the stiffness-enhancing reinforcement structure comprises windings.

6. The implant holder according to claim 5, wherein the reinforcement structure comprises adjacent each of the longitudinal ends more windings relative to the number of windings adjacent the middle portion.

7. The implant holder according to claim 5, wherein the reinforcement structure comprises adjacent each of the longitudinal ends thicker windings relative to the thickness of windings adjacent the middle portion.

8. The implant holder according to claim 1, wherein the cavity for occupation by the tubular implant structure is on at least one of its longitudinal ends joining another cavity.

9. The implant holder according to claim 1, wherein the cavity is substantially cylindrical or conical.

10. The implant holder according to claim 1, wherein the holder is a multiple part holder having at least two segments in use neighbouring each other in an axial direction.

11. The implant holder according to claim 1, wherein the cavity has an inner diameter which is substantially constant along the length of the cavity.

12. The implant holder according to claim 1, wherein the cavity has an inner diameter which varies along the length of the cavity.

13. The implant holder according to claim 1, wherein the implant-holder comprises substantially a tube.

14. The implant holder according to claim 1, wherein the tube has an outer diameter which is adjacent the longitudinal ends of the cavity larger than the outer diameter adjacent the middle portion of the cavity.

15. The implant holder according to claim 1, wherein the implant holder is associated with a first and a second fixture assembly for fixing respectively a first end portion of the implant holder to a first part of a fatigue test system and a second end portion of the implant holder to a second part of the fatigue test system.

16. The implant holder according to claim 15, wherein the first and second fixture assemblies are arranged to apply at least one mechanism selected from the group consisting of at least one force-fit mechanism and at least one form-fit mechanism.

17. The implant holder according to claim 15, wherein at least one of the first and second fixture assemblies further comprises: an insertable holder for inserting fittingly into one of the end portions of the implant holder: and at least one embracing holder for tightly embracing that one end of the implant holder that has the insertable holder inserted in it.

18. The implant holder according to claim 17, wherein the embracing holder comprises a substantially ring-shaped holder which fits around the end portion of the implant holder and which is provided with a tightening mechanism.

19. The implant holder according to claim 1, wherein the implant holder is associated with a preparation assembly for facilitating a clamping of the tubular implant structure in the implant holder in an axially compressed manner.

20. The implant holder according to claim 19, wherein the preparation assembly comprises a guider and two end portion holders which are fixable to the guider and moveable to and from each other along the guider, each of the end portion holders defining a recess for holding one end of the implant holder, so that the middle portion of the implant holder is elongatable upon enlargement of a distance between the end portion holders.

21. The implant holder according to claim 1, wherein at least a part of the implant holder is transparent.

22. The implant holder according to claim 1, wherein the implant holder is associated with a fatigue test system for repetitively deforming a substantially tubular implant structure which is within a radial range and within an axial range expandable and contractable and which has at least a first and a second end.

23. The implant holder according to claim 22, wherein the fatigue test system comprises at least a first and second part which are controllably moveable relative to each other, so that the tubular implant structure is subjected to axial elongation and/or axial compression.

24. The implant holder according to claim 22, wherein the fatigue test system is arranged for rotating first and second fixture assemblies relative to each other around an axis which coincides with the axis of the tubular implant structure when it is fixed to the system, so that in use the implant structure is subjected to torsion.

25. The implant holder according to claim 24, wherein the fatigue test system is further arranged for hinging in use the fixture assemblies within a predetermined imaginary plane upon movement of the fixture assemblies relatively to and from each other, so that in use the tubular implant structure is subjected to bending.

* * * * *